(12) United States Patent
Manjeshwar et al.

(10) Patent No.: US 7,312,455 B2
(45) Date of Patent: Dec. 25, 2007

(54) METHOD AND SYSTEM FOR SCATTER CORRECTION IN A POSITRON EMISSION TOMOGRAPHY SYSTEM

(75) Inventors: Ravindra Mohan Manjeshwar, Guilderland, NY (US); Floribertus Philippus Martinus Heukensfeldt Jansen, Ballston Lake, NY (US); Charles William Stearns, New Berlin, WI (US)

(73) Assignee: The General Electric Company, Schenectady, NY (US)

( * ) Notice: Subject to any disclaimer, the term of this patent is extended or adjusted under 35 U.S.C. 154(b) by 310 days.

(21) Appl. No.: 11/034,166

(22) Filed: Jan. 12, 2005

(65) Prior Publication Data

US 2006/0151705 A1 Jul. 13, 2006

(51) Int. Cl.
*G01T 1/164* (2006.01)
(52) U.S. Cl. .............................. 250/363.03
(58) Field of Classification Search ............ 250/363.03
See application file for complete search history.

(56) References Cited

U.S. PATENT DOCUMENTS 5,903,008 A * 5/1999 Li .......................... 250/363.04
6,631,284 B2 * 10/2003 Nutt et al. ................. 600/427
7,129,496 B2 * 10/2006 Stearns et al. ......... 250/363.03
2003/0161521 A1 * 8/2003 Newport et al. ............ 382/131
2005/0072929 A1 * 4/2005 Chuang et al. ........ 250/363.03
2007/0040122 A1 * 2/2007 Manjeshwar et al. .. 250/363.03

OTHER PUBLICATIONS

Bergstrom M, Eriksson L, Bohm C, Blomqvist G and Litton J, "Correction for Scattered Radiation in a Ring Detector Positron Camera by Integral Transformation of the Projections", Journal of Computer Assisted Tomography, Feb. 1983, pp. 42-50, vol. 7, No. 1.
Stearns C W, "Scatter Correction Method for 3D PET using 2D Fitted Gaussian Functions", Journal of Nuclear Medicine, 1995, pp. 105, vol. 36.
J. M. Ollinger, "Model-Based Scatter Correction for Fully 3D PET", Physics in Medicine and Biology, 1996, pp. 153-176, vol. 41.
S. D. Wollenweber, "Parameterization of a Model-Based 3-D PET Scatter Correction", IEEE Transactions in Nuclear Science, Jun. 2002, pp. 722-727, vol. 49, No. 3.
Watson C.C, "New Faster Image Based Scatter Correction for 3D PET", IEEE Transactions in Nuclear Science, Aug. 2000, pp. 1587-1594, vol. 47, No. 4.

* cited by examiner

*Primary Examiner*—David Porta
*Assistant Examiner*—Christine Sung
(74) *Attorney, Agent, or Firm*—The Small Patent Law Group LLP; Dean D. Small

(57) ABSTRACT

Methods and systems for providing scatter correction in a positron emission tomography (PET) system are provided. The method includes determining a look-up table of scatter sinograms during a PET acquisition scan period. The method further includes scatter correcting acquired scan data obtained during the PET acquisition scan period.

20 Claims, 8 Drawing Sheets

METHOD AND SYSTEM FOR SCATTER CORRECTION IN A POSITRON EMISSION TOMOGRAPHY SYSTEM

BACKGROUND OF THE INVENTION

The invention relates generally to positron emission tomography (PET) systems, and more particularly, to pre-computing a scatter sinogram look-up table during PET emission acquisition to correct for scatter.

PET scanners typically generate images depicting the distribution of positron-emitting nuclides in patients. The positron interacts with an electron in the body of the patient by annihilation, and then the electron-positron pair is converted into two photons. The photons are emitted in opposite directions along a line of response. The annihilation photons are detected by detectors that are placed on both sides of the line of response on a detector ring. The image is then generated based on the acquired emission data that includes the annihilation photon detection information.

A PET scanner typically includes a detector ring assembly including rings of detectors that encircle the patient. Coincidence detection circuits connect to the detectors and record only those photons that are detected within a narrow time window by detectors located on opposite sides of a line joining the detectors to the point of annihilation. These detections are deemed to have occurred "simultaneously" and termed coincidence events. The coincidence events indicate that a positron annihilations occurred along a line joining the two opposing detectors. The coincidence events detected by the PET detector ring assembly are typically stored within data structures called emission sinograms. An emission sinogram is a histogram of the detected coincidence events where each of a plurality of bins in the histogram represents a potential detector pair element. An image of the activity distribution within a patient's body is generated from the emission sinograms through a process called image reconstruction.

Some gamma rays are deflected from their original direction due to interaction with a body part before reaching the detectors. Such events are termed scatter events. It is desirable to reject the scatter events during the acquisition of emission sinograms, because the images generated using only the detected true coincidence events represent a true activity distribution of radio-activity in the scanned body part of the patient. Not rejecting the scatter events in the image reconstruction results in biased estimates of the activity distribution in the patient.

In order to correct for scattered coincidences in PET scanners, various scatter correction methods are known. One widely used scatter correction method, used for 2D PET acquisitions, involves making scatter estimates based on integral transforms of the emission data. However, the method does not always perform satisfactorily for 3D PET acquisitions where scatter fractions are much larger. For moderate levels of scatter, for example, as seen in brain scans (and smaller patients), scatter correction using function-fitting methods to the counts outside the object support has provided improved performance. However, for larger patients, the function-fitting methods are not robust enough as they over-estimate the scatter inside the object. Model based scatter correction methods generally perform well for patients of all sizes and 3D PET acquisitions. Known model-based scatter correction methods generally involve algorithms that use the measured PET emission and transmission sinograms to estimate the prevalence of scattered events. The output of these algorithms is the mean estimate of the scatter events, which are also stored into sinograms. The measured PET emission sinograms are corrected for scatter by subtracting the estimated scatter sinograms from the measured PET emission data. Therefore, the final reconstructed images are based mainly on true coincidence events and not on the scatter events.

However, known model based scatter correction algorithms use many simplifying assumptions that can reduce the accuracy of the scatter estimation model. Further, known model-based scatter correction methods are time consuming and involve intensive computations that are performed after the entire PET scan acquisition is completed because they use the measured emission data

BRIEF DESCRIPTION OF THE INVENTION

In an exemplary embodiment, a method for scatter correction in a positron emission tomography (PET) system is provided. The method includes determining a look-up table of scatter sinograms during a PET acquisition scan period. The method further includes scatter correcting the acquired scan data obtained during the PET acquisition scan period.

In another exemplary embodiment, a positron emission tomography (PET) system is provided. The PET system includes a PET scanner for performing a PET scan. The PET system further includes a processor configured to determine a look-up table of scatter sinograms during the PET scan using the PET scanner and to scatter correct the acquired scan data obtained during the PET scan.

DETAILED DESCRIPTION OF THE INVENTION

Various embodiments of the invention provide a method and system for reconstructing a PET image of a scanned object by computing a look-up table of scattered coincidence information as a function of spatial position in the object during the time period required for PET acquisition. This allows for correcting for scatter almost immediately, if not immediately, after the PET acquisition is completed. The computation of scatter look-up tables using, for example, modeling of the physics of scatter is performed during the PET acquisition scan period. The computed scatter look-up table enables a fast reconstruction of a PET image either by correcting the measured PET scan data for scatter prior to reconstruction or by using the scatter look-up table in an iterative image reconstruction loop and as described in more detail herein.

Figure 1:
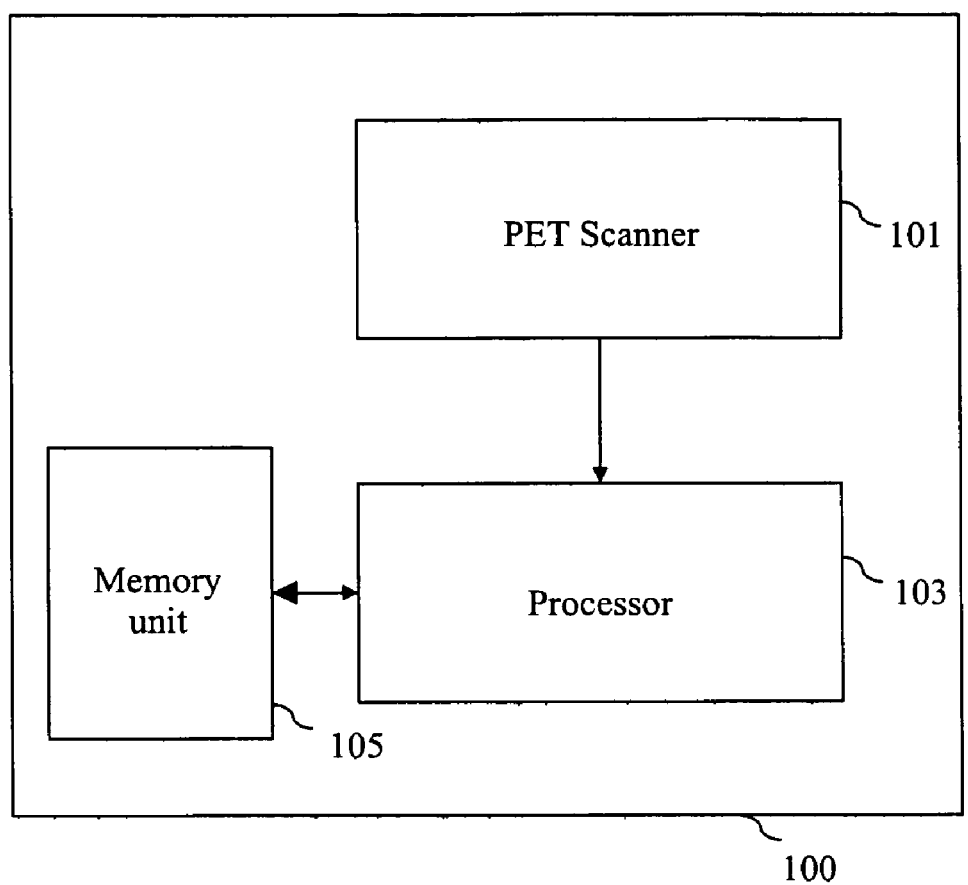
FIG. 1 is a block diagram showing a PET system in accordance with an exemplary embodiment of the invention.

FIG. 1 is a block diagram showing a PET system 100 in accordance with an exemplary embodiment of the invention. In this embodiment, PET system 100 includes a PET scanner 101. In another embodiment, PET system 100 includes a dual modality PET/CT scanner (not shown) that performs both computed tomography (CT) scans and PET scans of a patient. PET System 100 further includes a processor 103 and a memory unit 105. PET acquisition scan period of PET scanner 101 is divided into a transmission (e.g., CT scan or rotating rod source scan) portion and an emission portion. Transmission scan from a CT scanner typically lasts a few seconds and results in the generation of an image that represents the attenuation properties of the patient's scanned body part. The transmission scan portion of a PET only scanner 101 can also generate an image of the attenuation properties of the scanned body. This scan however can take 20-30 minutes. After the transmission scan is completed, the PET scanner 101 performs the emission scan. The PET emission scan typically lasts for 20-30 minutes regardless of whether the transmission image is generated using the CT portion of a PET/CT scanner or using a rotating rod source and a PET scanner.

Processor 103 performs computations in order to reconstruct an image of the patient's body part scanned by PET scanner 101. In various embodiments, processor 103 generates, during the emission portion of the PET acquisition scan period after the attenuation data has been obtained, a scatter look-up table containing estimated scatter sinograms as a function of spatial position in a body assuming uniform radioactivity distribution. Memory unit 105 stores the generated scatter look-up table. Processor 103 and memory 105 in one embodiment are embedded in PET scanner 101.

Figure 2:
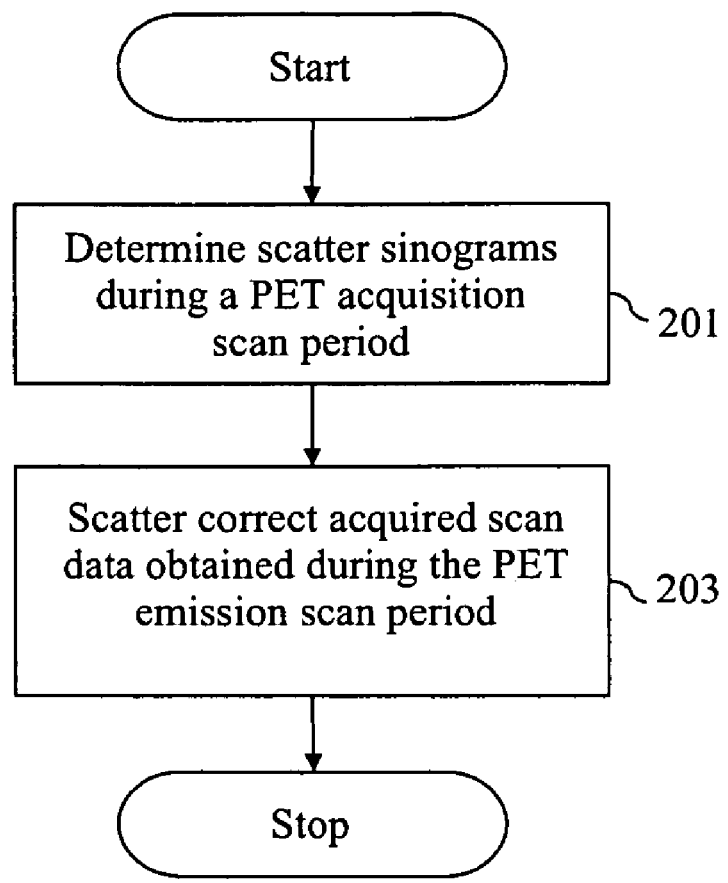
FIG. 2 is a flowchart illustrating a method for scatter correction in a PET system in accordance with an exemplary embodiment of the invention.

FIG. 2 is a flowchart illustrating a method for scatter correction in a PET system in accordance with an exemplary embodiment of the invention. At 201, scatter sinograms are determined during a PET acquisition scan period. A scatter sinogram includes the probabilistic estimate of scatter, which are determined using the tissue attenuation properties that are represented by the acquired attenuation image.

Specifically, an attenuation image of an object being scanned is obtained during the transmission period of a PET acquisition scan period or from a CT scan that precedes the PET emission acquisition. Using the attenuation image, and assuming a uniform radiotracer activity of one unit in each voxel of the image, scatter sinogram estimates for each voxel are obtained. The obtained scatter sinogram estimates are stored in a look-up table as a function of their spatial location or voxel index. In one embodiment, the look-up table is generated as a matrix and the scatter estimates are stored in the table on a voxel position basis. The rows of the matrix correspond to the voxel indices and the columns correspond to the obtained scatter sinogram estimates. In one embodiment, the number of rows in the look-up table matrix is equal to the number of voxels in the attenuation image and the number of columns is equal to the number of sinogram elements produced by PET scanner 101.

At 203, scan data obtained during the PET acquisition scan period is scatter corrected. Once the PET emission data is obtained, a measured scan image is generated. The measured image includes data corresponding to true coincidence events (coincidence data) as well as data corresponding to scatter events (scatter data). In various embodiments of the invention, an image of the true radio-activity image is generated by using the scatter sinogram look-up table for scatter correction. In one embodiment, the measured emission data is corrected for scatter before image reconstruction. In another embodiment, the measured emission data and the scatter look-up table are used during an iterative image reconstruction procedure to generate a "true" emission image.

Figure 3:
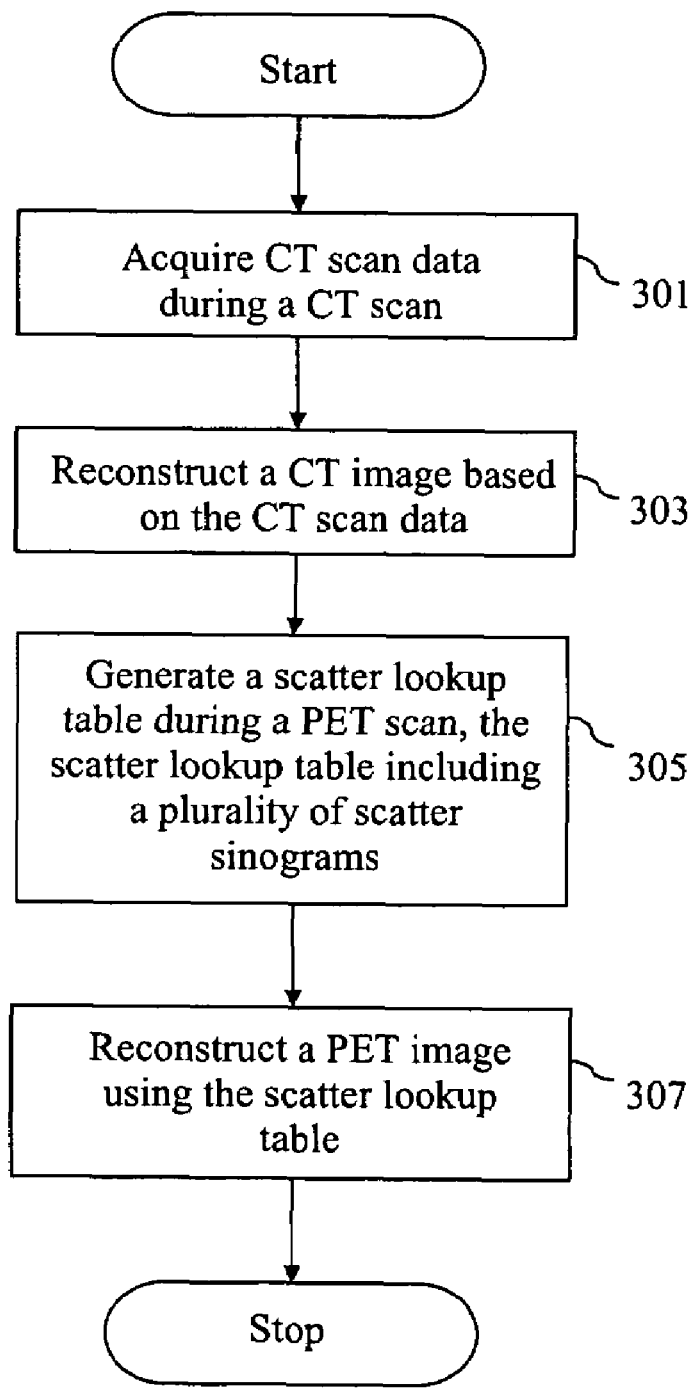
FIG. 3 is a flowchart illustrating a method for scatter correction in a PET system in accordance with another exemplary embodiment of the invention.

FIG. 3 is a flowchart illustrating a method for scatter correction in a PET system in accordance with another exemplary embodiment of the invention. At 301, CT scan data of the object being scanned is acquired during a CT scan period. In one embodiment, the CT scan of a dual modality PET/CT scanner corresponds to the transmission scan with a rotating rod source in a PET only scanner. At 303, a CT image is reconstructed using the acquired CT scan data. In one embodiment, the CT image is an attenuation image, which is down-sampled in order to lower its resolution. Lowering the resolution of the image decreases the number of voxels in the image.

At 305, a scatter look-up table that includes scatter sinograms for each voxel in the CT image is generated during the emission portion of the PET scan acquisition period. Because Compton scatter has predominantly low frequencies, the look-up table is generated using a down sampled low-resolution version of the CT image. The resolution or the number of voxels in the CT image determines the computational and memory requirements for the scatter look-up table. Therefore, by using a low resolution CT image, the computational time, as well as the memory required for storing the scatter look-up table, can be minimized.

At 307, the scatter look-up table is used to reconstruct an image of the scanned object. In one embodiment, the image is reconstructed using iterative or analytical image reconstruction algorithms as are known, which use PET scan acquisition data that has been pre-corrected for scatter.

In another embodiment, the image is reconstructed using an iterative image reconstruction algorithm as is known, which uses PET scan acquisition data that has not been pre-corrected for scatter. For example, the image can be reconstructed by satisfying the equation:

$$\lambda = P_{PET}F + S_{LUT}F + R \tag{1}$$

where
$\lambda$ is the measured emission sinogram;
$P_{PET}$ is the system transition matrix;
F is the image estimate;
$S_{LUT}$ is the scatter sinogram look-up table; and
R is the random sinogram.

During the image reconstruction process, an initial estimate of an image (F) of the scanned object and a system transition matrix ($P_{PET}$) is obtained. Next, $P_{PET}$ and the generated scatter look-up table ($S_{LUT}$) are scaled by F and added to the random sinogram (R). R is obtained using known algorithms. The obtained sum is compared to the measured emission sinogram ($\lambda$) during the emission portion of the PET scan acquisition period. A new estimate of F is obtained based on the results of the comparison using known algorithms. The scaling, summing and comparing operations are performed iteratively, until equation (1) is satisfied. Therefore, scatter correction is performed during the iterative image reconstruction process. This eliminates generation of excess noise, which results if scatter is corrected prior to image reconstruction.

It should be noted that in the various embodiments, the matrix $P_{PET}$ is not pre-computed, but is instead computed analytically "on-the-fly" during image reconstruction. In addition, model based scatter estimation techniques and the low spatial frequency nature of scatter are used to compute and store a reduced matrix $S_{LUT}$.

Figure 4:
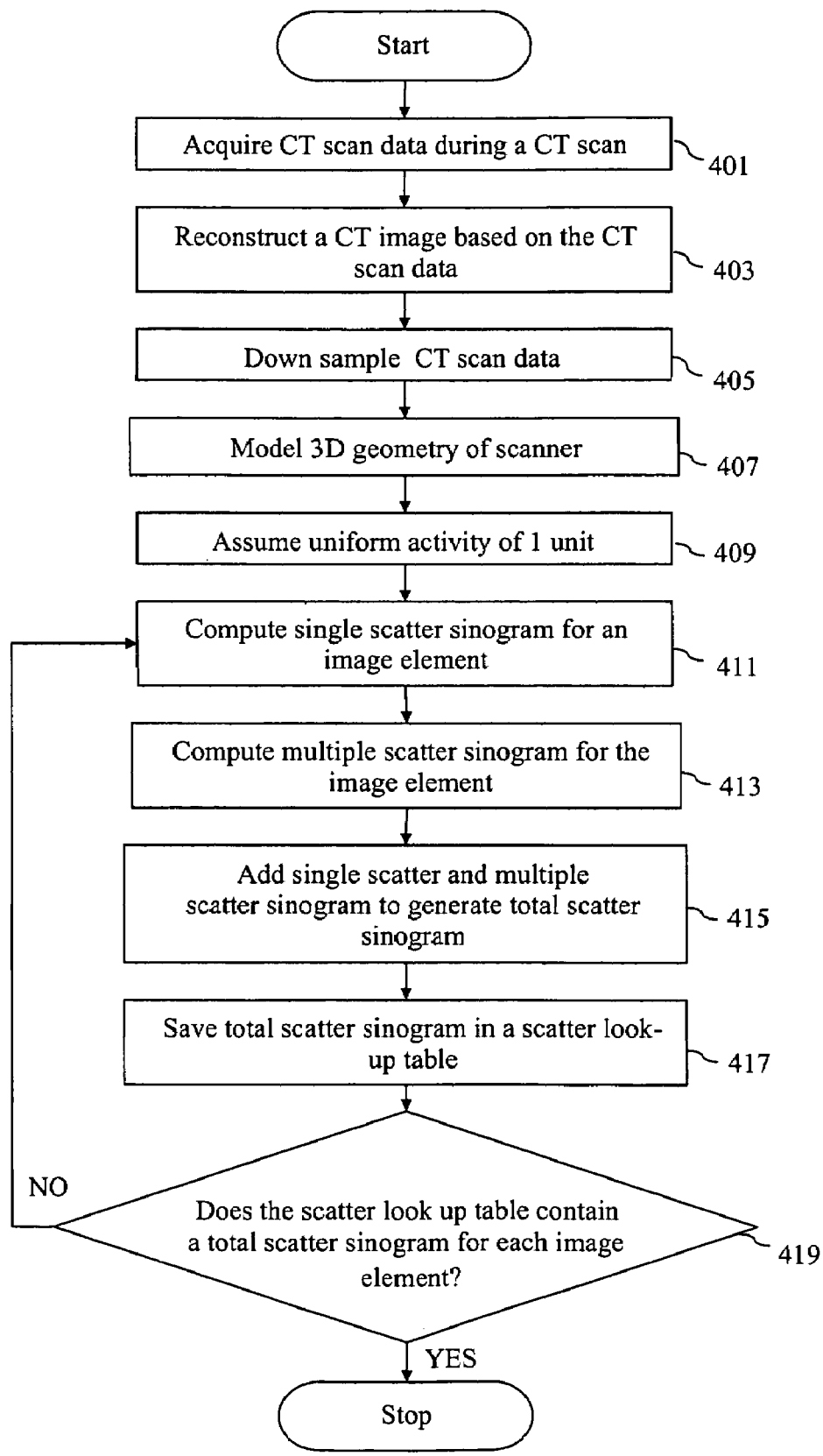
FIG. 4 is a flowchart illustrating a method for generating a scatter look-up table in accordance with an exemplary embodiment of the invention.

FIG. 4 is a flowchart illustrating a method for generating a scatter look-up table in accordance with an exemplary embodiment of the invention. At 401, CT scan data of an object being scanned is acquired during a CT scan period. At 403, a CT image of the object is reconstructed based on the acquired CT scan data as is known. At 405, the CT image is down-sampled in order to lower its resolution. Lowering the resolution of the image decreases the number of image elements, for example voxels, in the image.

At 407, 3D geometry of the scanner used for scanning the object is modeled as is known. At 409, a uniform radiotracer activity of one unit in each voxel of the CT image is assumed. At 411, a single scatter sinogram is computed for an image element using known methods. At 413, a multiple scatter sinogram is computed for the image element using known methods. At 415, the computed single and multiple scatter sinograms are summed to generate a total scatter sinogram for the image element. At 417, the total scatter sinogram is saved in a scatter look-up table. In various embodiments, the scatter look-up table is a series of total scatter sinograms wherein each sinogram represents the scatter sinogram generated by an individual image element, for example a pixel or a voxel, assuming all other image elements are inactive. Therefore, the number of scatter sinograms in the scatter look-up table is the same as the number of image elements in the CT image.

At 419, a determination is made as to whether the scatter look-up table contains a total scatter sinogram corresponding to every image element. If the scatter look-up table does not contain a total scatter sinogram corresponding to every image element, steps 411 to 419 are repeated for each of the image elements.

Figure 5A:
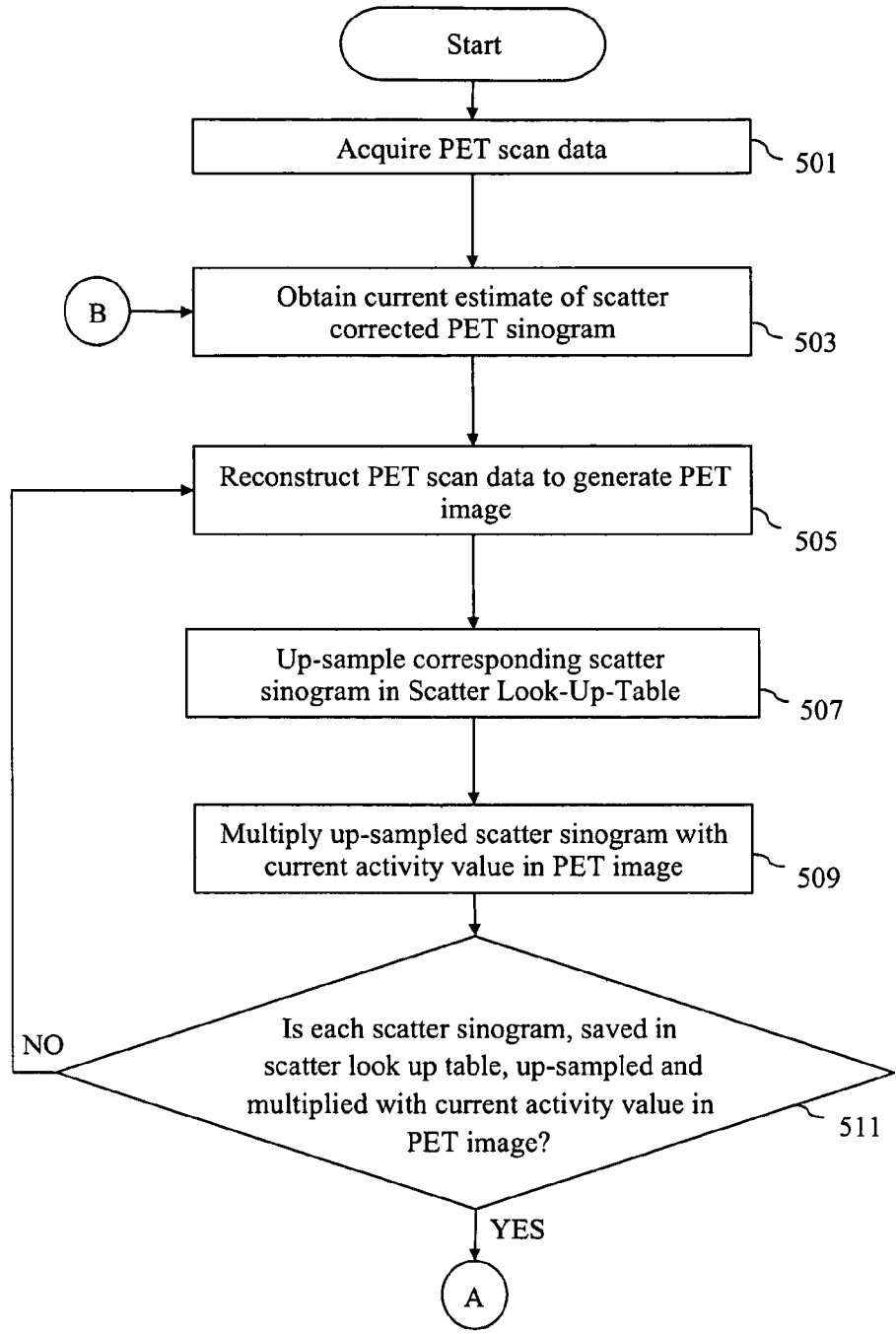
FIGS. 5A and 5B are a flowchart illustrating a method for scatter correction using a scatter look-up table in a PET system in accordance with an exemplary embodiment of the invention.
Figure 5B:
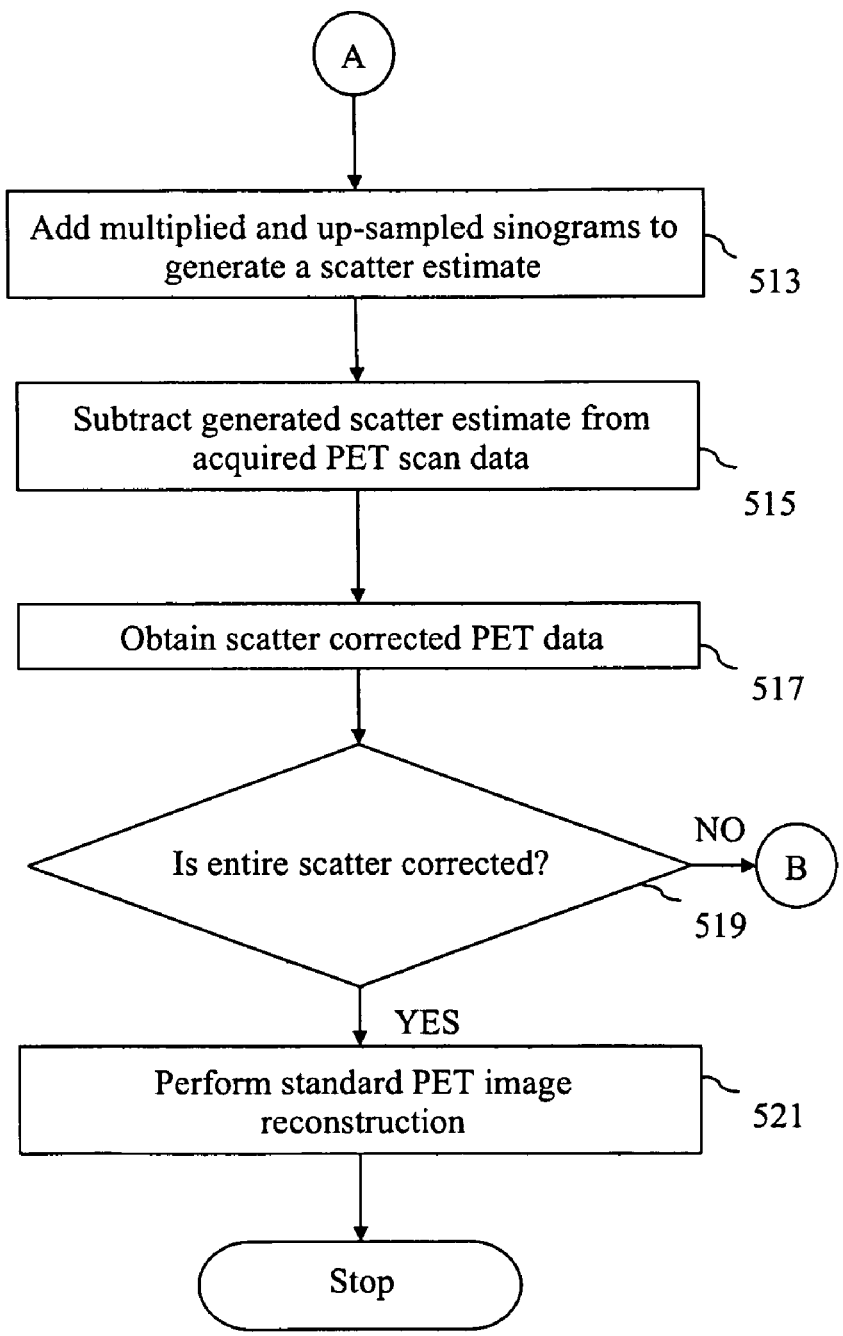

FIGS. 5A and 5B are a flowchart illustrating a method for scatter correction using a scatter look-up table in a PET system in accordance with an exemplary embodiment of the invention. At 501, PET scan data for an object being scanned is acquired. At 503, the current estimate of scatter corrected PET sinogram is set equal to the measured emission sinogram data. At 505, the PET scan data is reconstructed to form an estimate of the activity distribution image of the object being scanned.

At 507, each scatter sinogram saved in the scatter look-up table is up-sampled to have the same dimensions as the measured emission sinogram data. At 509, the up-sampled scatter sinogram is multiplied by the activity in the corresponding image element of the activity distribution image. At 511, a determination is made as to whether each scatter sinogram saved in the scatter look-up table has been up-sampled and multiplied by the activity in the corresponding image element of the activity distribution image. If not, step 509 is repeated.

If each sinogram has been up-sampled, then at 513, the up-sampled and multiplied sinograms are summed to form a total scatter estimate for the PET activity distribution image. At 515, the generated total scatter estimate is subtracted from the acquired PET scan data to obtain PET scan data, which has been corrected for scatter. Therefore, at 517, an initial scatter corrected PET scan data is obtained. At 519, a determination is made as to whether the entire scatter from the PET scan data has been corrected. If the entire scatter from the PET scan data has not been corrected, then steps 503 to 519 are repeated. If the entire scatter from the PET scan data has been corrected, then at 521, the final scatter corrected PET scan data is used to reconstruct a final activity distribution image of the scanned object.

Figure 6A:
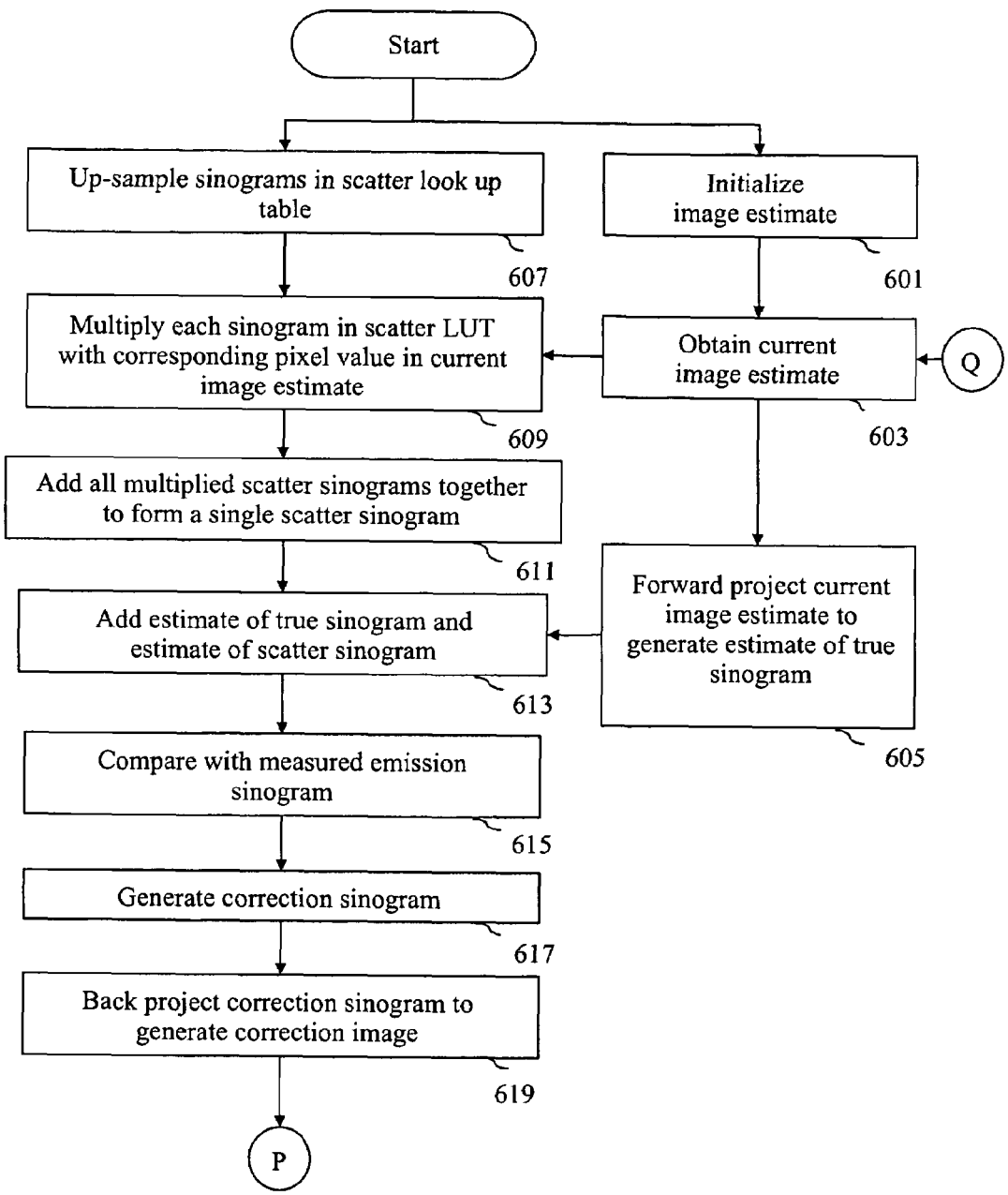
FIGS. 6A and 6B are a flowchart illustrating a method for scatter correction using a scatter look-up table in a PET system in accordance with another exemplary embodiment of the invention.
Figure 6B:
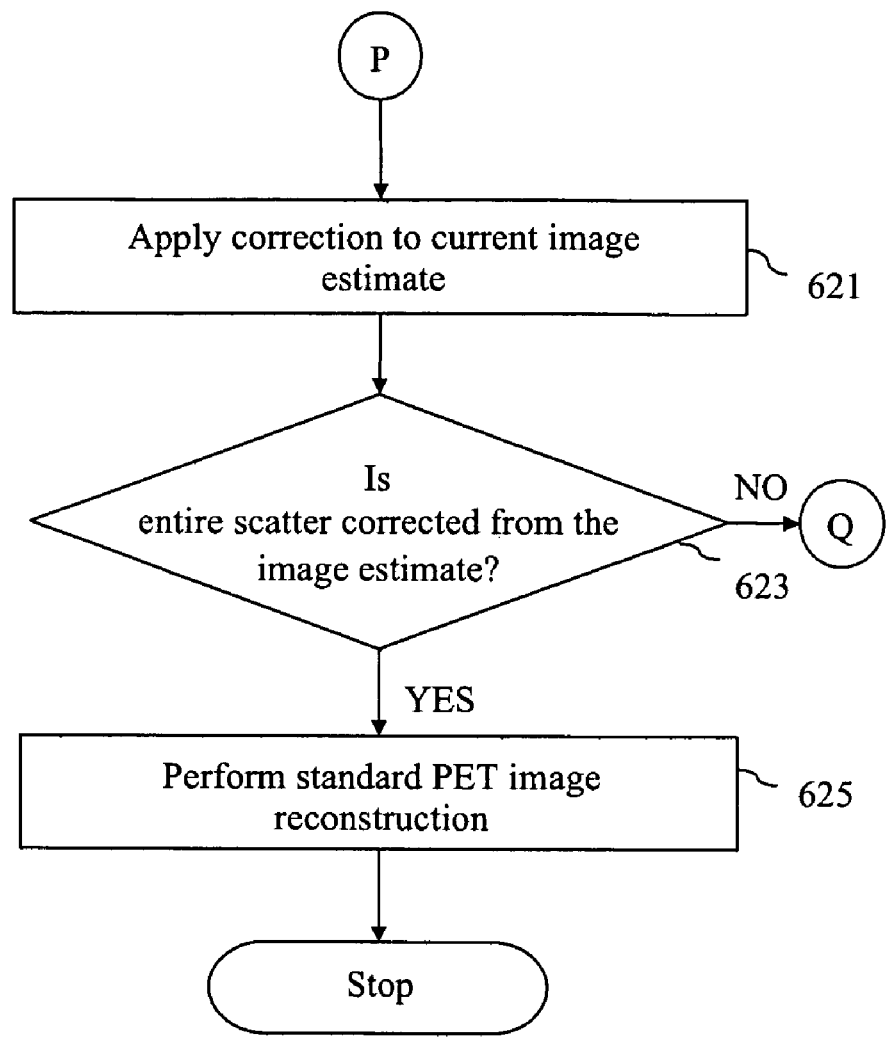

FIGS. 6A and 6B are a flowchart illustrating a method for scatter correction using a scatter look-up table in a PET system in accordance with another exemplary embodiment of the invention. At 601, an initial estimate of an activity distribution image of the scanned object is made. In various embodiments, this estimate depicts a uniform image or the image that is generated using a standard algorithm such as, for example, a filtered-back-projection algorithm.

At 603, a current image estimate of the scanned object is obtained. At 605, the activity distribution image estimate is forward projected to generate an estimate of a true coincidence sinogram. At 607, scatter sinograms saved in the scatter look-up table are up-sampled. At 609, each of the up-sampled sinograms saved in the scatter look-up table are multiplied by the activity in the corresponding image elements, obtained at 603, of the activity distribution image estimate. Next at 611, the sinograms are summed together to generate an estimated scatter sinogram.

At 613, the estimated scatter and true coincidence sinograms are added together to provide an estimate of the measured PET scan data containing both true and scatter coincidence events. At 615, the estimate of the measured PET scan data and the measured PET scan data are compared.

Thereafter at 617, an optimization routine is performed to generate a correction sinogram for the activity distribution image estimate. At 619, the correction sinogram is back projected to generate a correction activity distribution image estimate. At 621, the generated correction is applied to the current image estimate in order to reduce the dissimilarity between the estimate of the measured PET scan data and the measured PET data.

At 623, a determination is made as to whether the entire scatter from the measured PET scan data has been corrected. If the entire scatter from the measured PET scan data has not been corrected, then steps 605-623 are repeated. If the entire scatter from the measured PET scan data has been corrected, then at 625 PET image reconstruction as is known is performed to obtain a scatter corrected PET scan image of the scanned object.

The various embodiments of the invention provide for use of the PET scan acquisition period to generate a scatter look-up table. Therefore, the invention utilizes the emission period of the PET scan acquisition to perform, for example, the computationally intensive portions of the scatter modeling. This enables the reconstruction of the scan image to be performed more accurately and in a much shorter time period, for example, after the completion of the PET scan acquisition period.

Further, the various embodiments of the invention provide an improved image reconstruction method, which includes scatter correcting within an iterative image reconstruction process. This reduces or eliminates the excess image noise that results from scatter pre-correction.

Further, the various embodiments of the invention provide an improved image reconstruction method and system that allows for correcting out-of field-scatter.

A technical effect of various embodiments of the invention is to provide a scatter look-up table generated during PET scan acquisition period. Another technical effect of various embodiments of the invention is to provide image reconstruction of a scanned object without pre-correcting the PET scan data for scatter. Yet another technical effect of various embodiments of this invention is to provide image reconstruction of the scanned object with out-of-field scatter correction.

In various embodiments of the invention, the method of scatter correction can be implemented in software, hardware, or a combination thereof. The methods provided by various embodiments of the present invention, for example, can be implemented in software by using standard programming languages such as, for example, C, C++ and Java.

In various embodiments of the invention, the methods of scatter correction as described herein or any of its components may be embodied in the form of a processing machine. Typical examples of a processing machine include a general-purpose computer, a programmed microprocessor, a digital signal processor (DSP), a micro-controller, a peripheral integrated circuit element, and other devices or arrangements of devices, which are capable of implementing the steps that constitute the methods described herein.

The processing machine executes a set of instructions (e.g., corresponding to the method steps described herein) that are stored in one or more storage elements (also referred to as computer usable medium). The storage element may be in the form of a database or a physical memory element present in the processing machine. The physical memory can be, for example, but not limited to, an electronic, magnetic, optical, electromagnetic, infrared, or semiconductor system, apparatus, device, or propagation medium. More specific examples of the physical memory include, but are not limited to, the following: a random access memory (RAM) a read-only memory (ROM), an erasable programmable read-only memory (EPROM or Flash memory), a Hard Disc Drive (HDD) and a compact disc read-only memory (CDROM).

The set of instructions may include various instructions that instruct the processing machine to perform the steps that constitute the method of scatter correction in a PET system as described herein. The set of instructions may be in the form of a program or software. The software may be in various forms such as system software or application software. Further, the software may be in the form of a collection of separate programs, a program module with a larger program or a portion of a program module. The software also may include modular programming in the form of object-oriented programming. The processing of input data by the processing machine may be in response to user commands, or in response to results of previous processing or in response to a request made by another processing machine.

While the invention has been described in terms of various specific embodiments, those skilled in the art will recognize that the invention can be practiced with modification within the spirit and scope of the claims.

What is claimed is:

1. A method for scatter correction in a positron emission tomography (PET) system, said method comprising:
    determining a look-up table of scatter sinograms during a PET acquisition scan period; and
    scatter correcting acquired scan data obtained during the PET acquisition scan period to reconstruct a PET image based on the scan data.

2. A method in accordance with claim 1 wherein the determining comprises calculating scatter probabilities during the PET acquisition scan period.

3. A method in accordance with claim 2 further comprising generating a scatter look-up table based on the calculated scatter probabilities.

4. A method in accordance with claim 1 wherein the scatter sinograms are determined during an emission portion of the PET acquisition scan period.

5. A method in accordance with claim 1 further comprising obtaining attenuation data during a transmission portion of the PET acquisition scan period by generating an attenuation image, the attenuation data used to generate the look-up table of scatter sinograms.

6. A method in accordance with claim 1 wherein the PET system is configured to perform x-ray computed tomography (CT) imaging and further comprising obtaining attenuation data from a CT acquisition, the attenuation data used to generate the look-up table of scatter sinograms.

7. A method in accordance with claim 1 wherein the scatter sinograms are stored in the look-up table as a function of spatial location.

8. A method in accordance with claim 1 further comprising performing an iterative image reconstruction process using pre-corrected scan data corrected using the determined scatter sinograms.

9. A method in accordance with claim 1 further comprising generating the scatter look-up table based on scatter probabilities calculated during the PET acquisition scan period and using the scatter look-up table to provide Scatter correction during an iterative image reconstruction process.

10. A method in accordance with claim 1 further comprising generating the scatter look-up table based on scatter probabilities calculated during the PET acquisition scan period and wherein the look-up table is configured on a voxel position basis.

11. A method in accordance with claim 1 further comprising generating the scatter look-up table based on scatter probabilities calculated during the PET acquisition scan period and scaling values within the look-up table after the PET acquisition scan period and based on scan information acquired during an emission portion of the PET acquisition scan period.

12. A method in accordance with claim 1 further comprising performing iterative image reconstruction in accordance with:

$$\lambda = P_{PET}F + S_{LUT}F + R$$

wherein $\lambda$ defines a measured emission sinogram, $P_{PET}$ defines a system transition matrix value, F defines an image estimate value, $S_{LUT}$ defines a scatter look-up table value, and R defines a random sinogram value.

13. A method of performing scatter correction in a positron emission tomography/computed tomography (PET/CT) system, said method comprising:
    acquiring CT scan data during a CT scan;
    reconstructing a CT image based on the CT scan data;
    generating a scatter look-up table during a PET scan, the scatter look-up table including a plurality of scatter sinograms; and
    reconstructing a PET image using the scatter look-up table.

14. A method in accordance with claim 13 further comprising calculating scatter probabilities during the PET scan.

15. A method in accordance with claim 13 wherein the reconstructing comprises using pre-corrected scan data corrected using the scatter look-up table.

16. A method in accordance with claim 13 wherein the generating comprises calculating scatter probabilities.

17. A method in accordance with claim 13 wherein the reconstruction is performed in accordance with:

$$\lambda = P_{PET}F + S_{LUT}F + R$$

wherein λ defines a measured emission sinogram, $P_{PET}$ defines a system transition matrix value, P defines an image estimate value, $S_{LUT}$ defines a scatter look-up table value, and R defines a random sinogram value.

18. A method in accordance with claim 13 wherein the look-up table is configured as sinogram scatter sinograms arranged on a voxel basis.

19. A positron emission tomography (PET) system comprising:
a PET scanner for performing a PET scan; and
a processor configured to determine a look-up table of scatter sinograms during a PET scan using the PET scanner and to scatter correct acquired scan data obtained during the PET scan.

20. A PET system in accordance with claim 19 further comprising a memory for storing the scatter look-up table including a plurality of scatter sinograms calculated during the PET scan.

* * * * *